US005619428A

United States Patent [19]
Lee et al.

[11] Patent Number: 5,619,428
[45] Date of Patent: Apr. 8, 1997

[54] METHOD AND APPARATUS FOR INTEGRATING AN AUTOMATED SYSTEM TO A LABORATORY

[75] Inventors: Shih-Jong J. Lee, Bellevue; Dayle G. Ellison; Chih-Chau L. Kuan, both of Redmond; Seho Oh, Mukilteo; Paul S. Wilhelm, Kirkland, all of Wash.

[73] Assignee: NeoPath, Inc., Redmond, Wash.

[21] Appl. No.: 455,388

[22] Filed: May 31, 1995

[51] Int. Cl.[6] .................................................. G01B 9/04
[52] U.S. Cl. ..................... 364/551.01; 382/128; 382/133
[58] Field of Search ........................... 364/551.01, 555, 364/497, 413.01, 413.08, 413.1; 250/461.2; 356/39, 372, 375, 380, 400, 401; 377/10, 11; 382/133, 128, 134; 436/43–48, 50, 55, 63, 8; 348/79; 395/924

[56] References Cited

U.S. PATENT DOCUMENTS

| | | | |
|---|---|---|---|
| 3,699,336 | 10/1972 | Ehrlich et al. | 250/461.2 |
| 3,824,393 | 7/1974 | Brain | 250/222.1 |
| 3,883,398 | 5/1975 | Ono | 435/305.3 |
| 3,916,176 | 10/1975 | Alien et al. | 364/413.1 |
| 4,045,655 | 8/1977 | Suzuki et al. | 377/10 |
| 4,097,845 | 6/1978 | Bacus | 382/134 |
| 4,129,854 | 12/1978 | Suzuki et al. | 382/134 |
| 4,150,360 | 4/1979 | Kopp et al. | 382/133 |
| 4,175,860 | 11/1979 | Bacus | 356/39 |
| 4,210,419 | 7/1980 | Castleman | 436/46 |
| 4,213,036 | 7/1980 | Kopp et al. | 382/133 |
| 4,315,309 | 2/1982 | Coli | 364/413.02 |
| 4,513,438 | 4/1985 | Graham et al. | 382/134 |
| 4,523,278 | 6/1985 | Reinhardt et al. | 364/413.1 |
| 4,596,464 | 6/1986 | Hoffman et al. | 356/336 |
| 4,620,548 | 11/1986 | Hasselbrack | 128/758 |
| 4,965,725 | 10/1990 | Rutenberg | 364/413.1 |
| 5,073,857 | 12/1991 | Peters et al. | 382/133 |
| 5,137,710 | 8/1992 | Smalley et al. | 435/40.52 |
| 5,235,522 | 8/1993 | Bacus | 364/497 |
| 5,257,182 | 10/1993 | Luck et al. | 364/413.1 |
| 5,268,966 | 12/1993 | Kasdan | 382/133 |
| 5,282,149 | 1/1994 | Grandone et al. | 364/497 |
| 5,287,272 | 2/1994 | Rutenberg et al. | 364/413.01 |
| 5,313,532 | 5/1994 | Harvey et al. | 382/156 |
| 5,315,700 | 5/1994 | Johnston et al. | 395/163 |
| 5,361,140 | 11/1994 | Hayenga et al. | 358/446 |
| 5,437,838 | 8/1995 | DeMoraville et al. | 364/497 |
| 5,473,706 | 12/1995 | Bacus et al. | 382/133 |
| 5,499,097 | 3/1996 | Ortyn et al. | 356/372 |

OTHER PUBLICATIONS

Bacus, James W. and Les J. Grace, "Optical Microscope System For Standardized Cell Measurements and Analyses", *Applied Optics*, 26:16, pp. 3280–3293, 15 Aug. 1987.

Bartels, Peter H. et al., "A Self–Learning Computer Program for Cell Recognition", *ACTA Cytologica: The Journal of Clinical Cytology*, 14:8, pp. 486–494, Oct. 1970.

(List continued on next page.)

*Primary Examiner*—Emanuel T. Voeltz
*Assistant Examiner*—Hal D. Wachsman
*Attorney, Agent, or Firm*—Leone & Moffa, P.A.

[57] ABSTRACT

An automated biological screening system obtains biological and procedural data from a slide set of a selected clinical laboratory. The integration system tests the data on standardized criteria and passes and fails the data in selected categories. The results of the assessment are used to make process adjustment recommendations based on the results of a laboratory process adjustment procedure. Assessment and adjustment may continue until data from a slide set from the selected clinical laboratory passes in each category. The integration system then sets up, calibrates and installs the automated biological screening system. During operation, the integration system continuously monitors biological data generated by the automated biological screening system. The biological data may also be stored in a central product/service database for additional monitoring. The integration system also serves as an objective standard for reviewing and improving laboratory practices.

52 Claims, 11 Drawing Sheets

OTHER PUBLICATIONS

Bartels, Peter H., "Numerical Evaluation of Cytologic Data VII. Multivariate Significance Tests", *Analytical and Quantitative Cytology*, vol. 3, No. 1, pp. 1–8, Mar. 1981.

Lee, James S. et al., "A Processing Strategy for Automated Papanicolaou Smear Screening", *Analytical and Quantitative Cytology and Histology*, The International Academy of Cytology, 14:5, pp. 415–425, Oct. 1992.

Tanaka, Noboru et al., "Automated Cytologic Screening System (CYBEST Model 4): an Integrated Image Cytometry System", *Applied Optics*, vol. 26, No. 16, pp. 3301–3307, Aug. 15, 1987. Copyright © 1987 by the Optical Society of America.

Duda, Richard O. and Peter E. Hart, "Fisher's Linear Discriminant", *Patent Classification and Scene Analysis*, Copyright ©1973, pp. 114–119.

Weber, J.E. et al., "Fuzzy Reasoning, Possibility Theory and Probability Theory in Expert Systems for Histopathology", Proceedings, Ninth Annual IEEE Conference on Engineering in Medicine and Biomedical Sciences, Boston, pp. 1560–1561, ©1987.

Wied, G.L. et al., "Expert Systems as Classifiers in Diagnostic Cytopathology", IEEE/Ninth Annual Conference of the Engineering in Medicine and Biology Society, pp. 1915–1917, ©1987.

Wied, G.L. et al., "Expert System Design Under Uncertainty of Human Diagnosticians", IEEE/Eighth Annual Conference of the Engineering in Medicine and Biology Society, pp. 757–760, ©1986.

Wied, G.L. et al., "Ticas–Stratex, an Expert Diagnostic System For Stratified Cervical Epithelium", IEEE/Ninth Annual Conference of the Engineering in Medicine and Biology Society, pp. 1557–1559, ©1987.

Serra, J., *Image Analysis and Mathematical Morphology*, pp. 372–423, Academic Press, 1982.

Smith, Warren J., "Image Evaluation", *Modern Optical Engineering: The Design of Optical Systems*, McGraw–Hill Book Company, 1966, pp. 308–325.

Patten, Jr., Stanley, "Diagnostic Cytopathology of the Uterine Cervix", Basel, Switzerland, Publisher: S. Karger, 1969, 2nd Edition 1978, Third volume in *Monographs in Clinical Cytology*, edited by G.L. Wied, pp. 10–15.

Kurman, Robert J. et al., "Part 1: Specimen Adequacy and Part 2: Descriptive Diagnosis", *The Bethesda System for Reporting Cervical/Vaginal Cytologic Diagnoses*, © 1994 Springer–Verlag.

Dytch, Harvey E. et al., "An Interactive Microcomputer-–Based System for the Quantitative Analysis of Stratified Tissue Sections", *Analytical and Quantitative Cytology and Histology*, vol. 9, No. 1, pp. 69–78, Mar. 1987.

Enslein, Kurt and Peter W. Neurath, "Augmented Stepwise Discriminant Analysis Applied to Two Classification Problems in the Biomedical Field", *Computers and Biomedical Research*, 2, 568–581 (1969).

Breiman, Leo "Chapter 2: Introduction To Tree Classification", pp. 18–58, *Classification and Regression Trees*, Wadsworth & Brooks/Cole Advanced Books & Software, Pacific Grove, California, 1984.

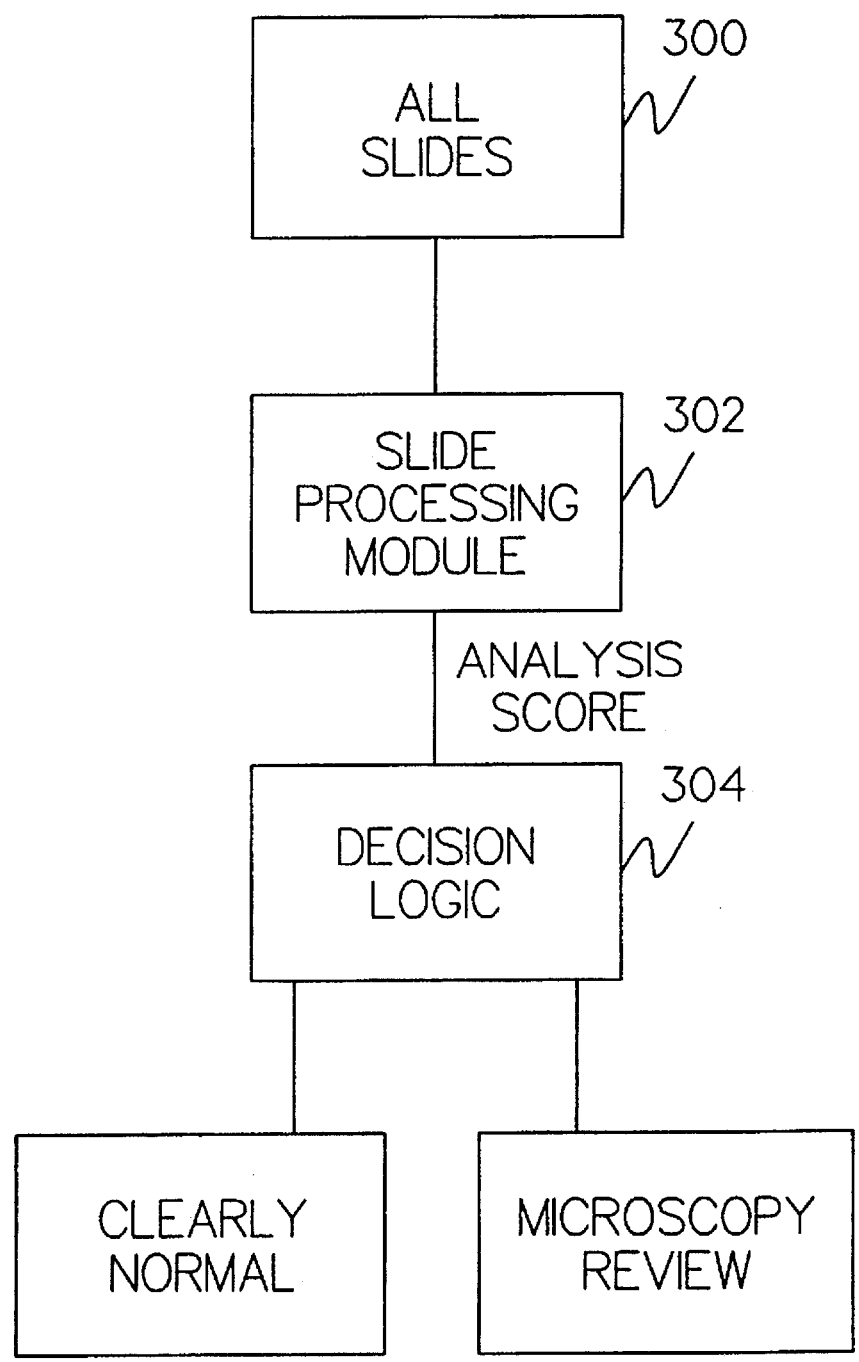
Fig_2

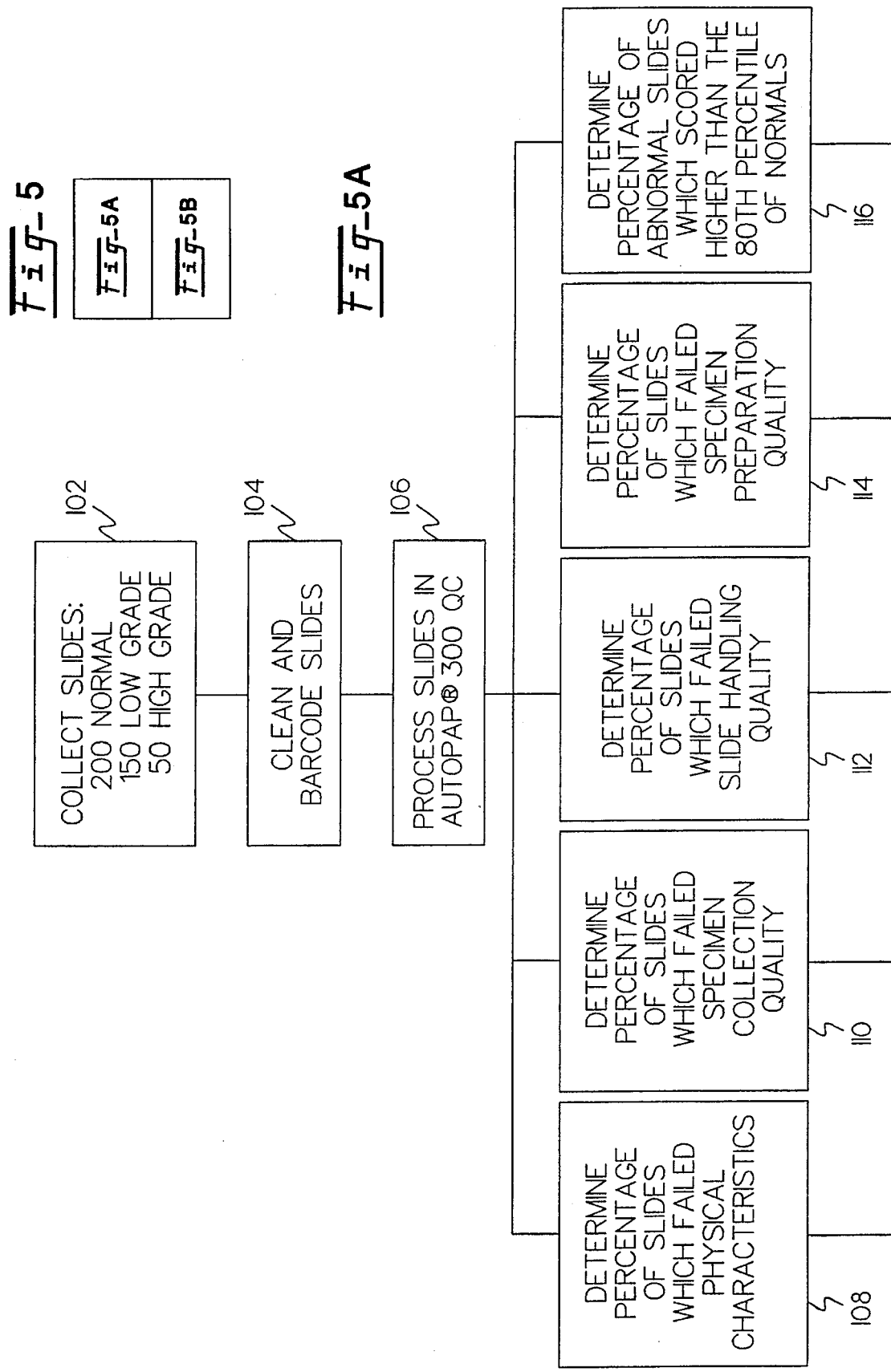

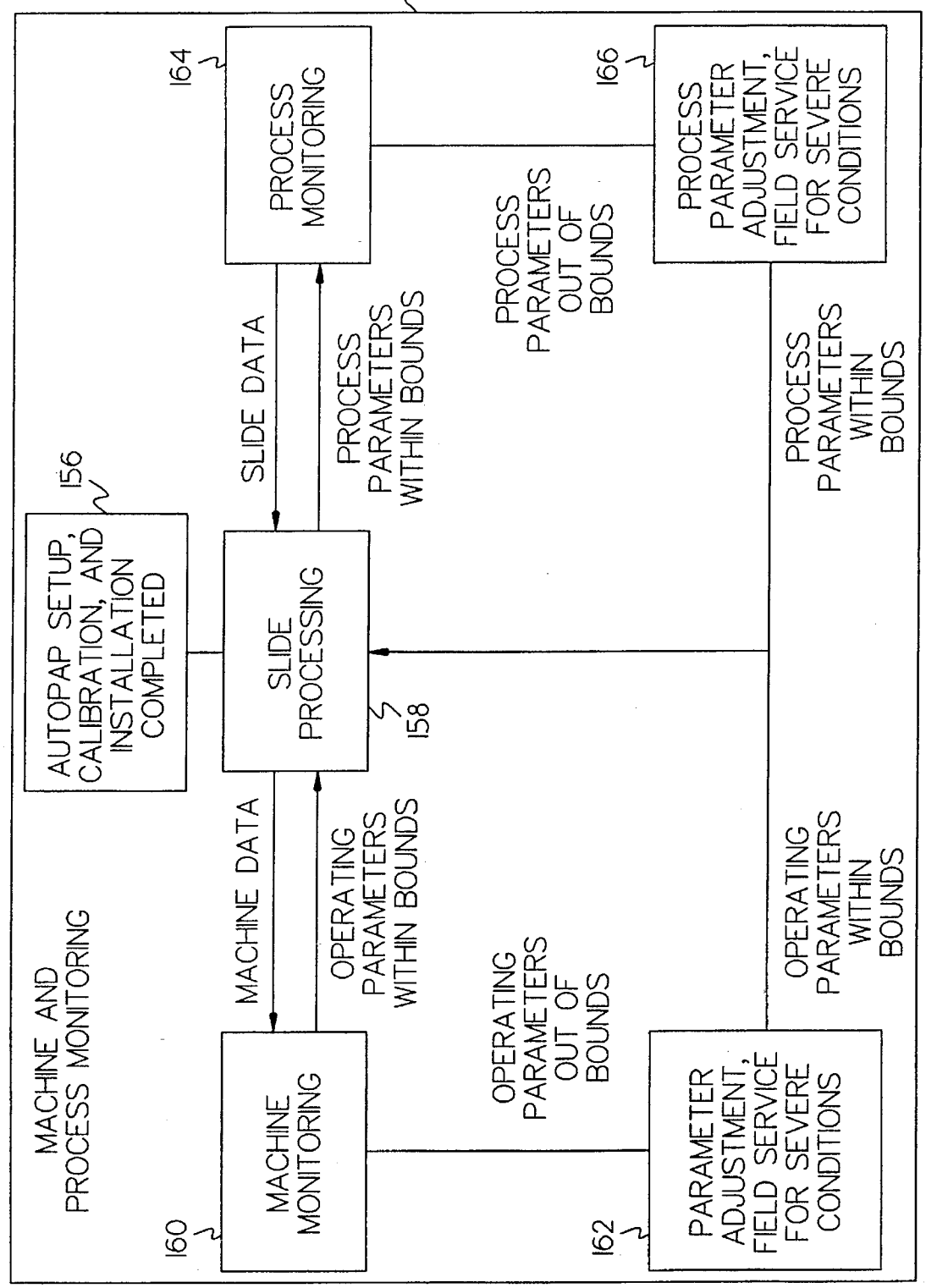

METHOD AND APPARATUS FOR INTEGRATING AN AUTOMATED SYSTEM TO A LABORATORY

This invention relates to a method and apparatus for integrating an automated system to a clinical laboratory, and more particularly to a method and apparatus for integrating an automated biological screening system to a clinical laboratory.

BACKGROUND OF THE INVENTION

Clinical laboratories vary widely in slide and patient populations, sampling and fixation methods, and staining protocols. As a result, significant variations may occur in the cellular presentation of biological specimens such as cervical Pap smears. Although biological specimen screening systems, such as the AutoPap® 300 System available from NeoPath, Inc. of Redmond, Wash., may be designed to normalize intra-laboratory and inter-laboratory variations to accommodate specimen population, sampling, and preparation differences, some laboratories may have variations that fall outside the designed operating range of a biological specimen screening system. Consistent automated evaluation accounting for the wide range of variation requires detection of these variations during the initial calibration, installation and normal use of the biological specimen screening system.

Assessing and optimizing laboratory practices enables introduction of an automated biological specimen screening system to a broader base of clinical laboratories. Once introduced, laboratory process and machine monitoring procedures can be used to maintain the effectiveness of a system in a clinical laboratory. These procedures increase the effectiveness of integrating a biological specimen screening system into a laboratory. These procedures provide an objective quality assessment of a laboratory's preparation and clinical practices.

It is therefore a motivation of the invention to provide an automated system for assessing, optimizing and monitoring the effectiveness of a biological specimen screening system in routine laboratory practice and to integrate an automated biological screening system to a clinical laboratory.

SUMMARY OF THE INVENTION

The invention provides a method and apparatus for integrating an automated biological screening system to a laboratory. The method begins by obtaining a slide set from the laboratory. Evaluation of the slide set provides a measurement of laboratory operating parameters. Laboratory procedures may then be adjusted if required, based upon the measurement of laboratory operating procedures. The method provides for calibration of the automated biological screening system according to the laboratory operating parameters. The method further provides for dynamic monitoring of the automated biological screening system and laboratory operating parameters during operation.

The invention comprises an automated biological screener for providing a biological data output. A data processor is connected to receive the biological data output and provides an assessment of laboratory procedure. The data processor provides process adjustment recommendations from a databank comprising a list of standard laboratory procedures. The invention further provides for setup, calibration and installation of the automated biological screening system according to laboratory parameters. System integrity checks, laboratory process monitors and a user interface provide for monitoring of the automated biological screener and laboratory operating parameters during operation.

The invention also provides a method of monitoring an automatic biological screening system comprising the steps of measuring at least one machine operating parameter, at intervals, based on at least one recent slide set processed by the automatic biological screening system to provide at least one operating parameter.

The invention also provides a method of monitoring an automatic biological screening system in a laboratory comprising the steps of measuring at least one laboratory process parameter, at intervals, based on at least one recent slide processed by the automatic biological screening system to provide at least one laboratory process monitoring parameter.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

FIG. 2 shows a process flow diagram of the slide sorting data flow.

FIG. 8 shows a flow diagram of machine and process monitoring of the invention.

DETAILED DESCRIPTION OF THE PREFERRED EMBODIMENT

Figure 1A:
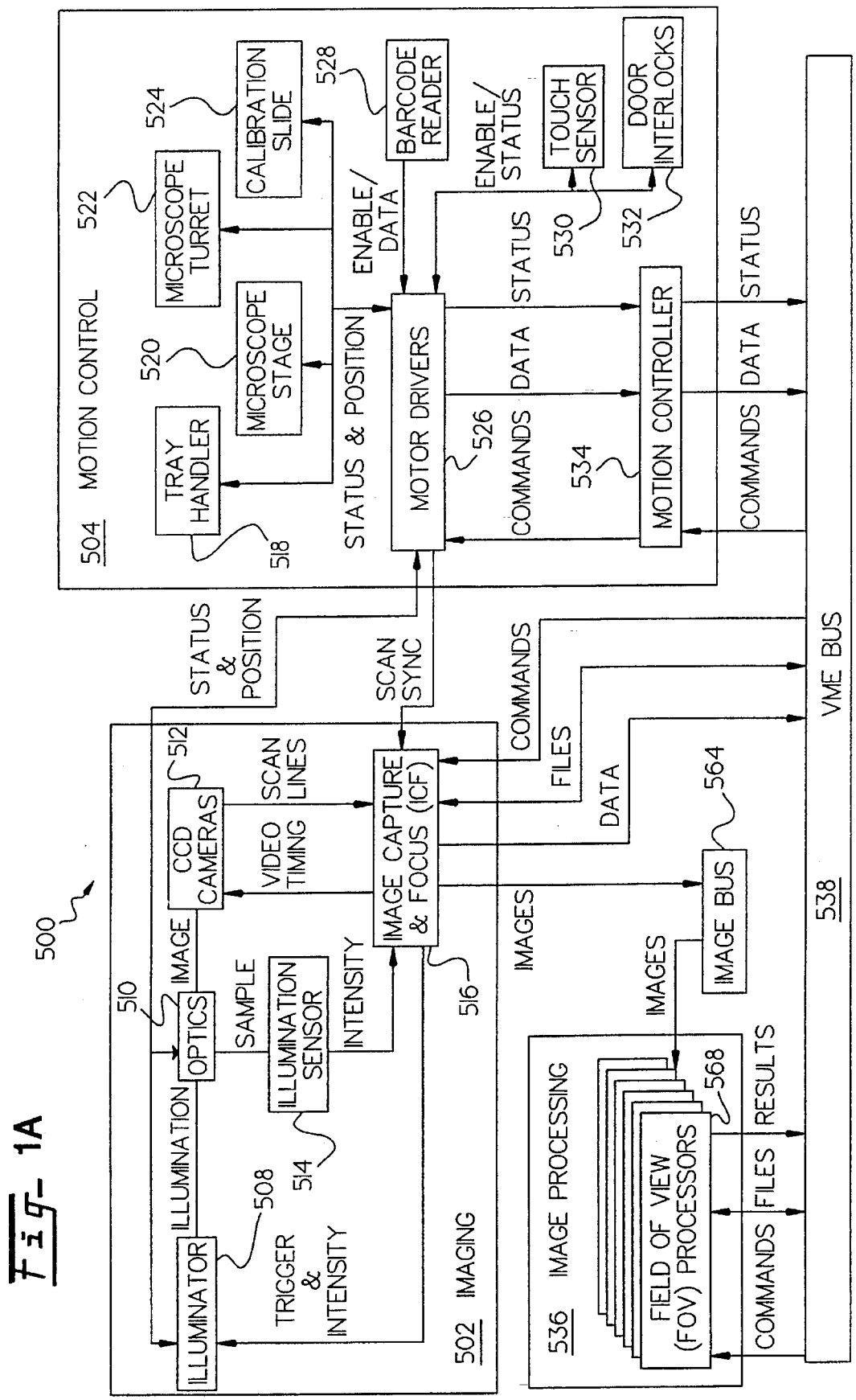
FIGS. 1A, 1B and 1C show the interactive biological specimen classification system of the invention.

In a presently preferred embodiment of the invention, the automated system disclosed herein is a system for analyzing cervical pap smears, such as that shown and disclosed in pending U.S. patent application Ser. No. 08/571,686, filed Dec. 13, 1995 which is a continuation of abandoned U.S. patent application Ser. No. 07/838,064, entitled "Method For Identifying Normal Biomedical Specimens", by Alan C. Nelson, et al., filed Feb. 18, 1992; U.S. Pat. No. 5,528,703, which is a continuation in part of abandoned U.S. patent application Ser. No. 07/838,395, entitled "Method For Identifying Objects Using Data Processing Techniques", by S. James Lee, et al., filed Feb. 18, 1992; U.S. Pat. No. 5,315,700, entitled "Method And Apparatus For Rapidly Processing Data Sequences", by Richard S. Johnston et al.; U.S. Pat. No. 5,361,140 entitled "Method and Apparatus for Dynamic Correction of Microscopic Image Signals" by Jon W. Hayenga et al.; and pending U.S. patent application Ser. No. 08/302,355, filed Sep. 7, 1994 entitled "Method and Apparatus for Rapid Capture of Focused Microscopic Images" to Hayenga et al., which is a continuation-in-part of abandoned application Ser. No. 07/838,063 filed on Feb. 18, 1992; the disclosures of which are incorporated herein, in their entirety, by the foregoing references thereto.

The present invention is also related to biological and cytological systems as described in the following patent applications which are assigned to the same assignee.

The present invention is also related to biological and cytological systems as described in the following patent applications which are assigned to the same assignee as the present invention, filed on Sep. 20, 1994 (unless otherwise noted), and which are all hereby incorporated by reference including pending U.S. patent application Ser. No. 08/309, 118 to Kuan et al. entitled, "Field Prioritization Apparatus and Method,"; pending U.S. patent application Ser. No. 08/309,061 to Wilhelm et al., entitled "Apparatus for Automated Identification of Cell Groupings on a Biological Specimen,"; pending U.S. patent application Ser. No. 08/309,116 to Meyer et al. entitled "Apparatus for Automated Identification of Thick Cell Groupings on a Biological Specimen,"; abandoned U.S. patent application Ser. No. 08/309,115 to Lee et al. entitled "Biological Analysis System Self Calibration Apparatus,"; pending U.S. patent application Ser. No. 08/308,992 to Lee et al. entitled "Apparatus for Identification and Integration of Multiple Cell Patterns,"; pending U.S. patent application Ser. No. 08/309,063 to Lee et al. entitled "A Method for Cytological System Dynamic Normalization,"; pending U.S. patent application Ser. No. 08/309,248 to Rosenlof et al. entitled "Method and Apparatus for Detecting a Microscope Slide Coverslip,"; U.S. patent application Ser. No. 08/309,077 now U.S. Pat. No. 5,566,249 to Rosenlof et al.

entitled "Apparatus for Detecting Bubbles in Coverslip Adhesive,"; pending U.S. patent application Ser. No. 08/309,931 to Lee et al. entitled "Cytological Slide Scoring Apparatus,"; pending U.S. patent application Ser. No. 08/309,148 to Lee et al. entitled "Method and Apparatus for Image Plane Modulation Pattern Recognition"; pending U.S. patent application Ser. No. 08/309,250 to Lee et al. entitled "Apparatus for the Identification of Free-Lying Cells,"; pending U.S. patent application Ser. No. 08/309,117 to Wilhelm et al., entitled "Method and Apparatus for Detection of Unsuitable Conditions for Automated Cytology Scoring"; pending U.S. patent application Ser. No. 08/309, 249, filed Sep. 20, 1994, entitled "Biological Specimen Analysis System Processing Integrity Checking Apparatus" to Ortyn et al.; pending U.S. patent application Ser. No. 08/303,179, filed Sep. 8, 1994, entitled "Cytological System Illumination Integrity Checking Apparatus and Method," to Ortyn et al.; U.S. patent application Ser. No. 08/309,078 now U.S. Pat. No. 5,581,631, filed Sep. 20, 1994, entitled "Cytological System Image Collection Integrity Checking Apparatus," to Ortyn et al.; U.S. patent application Ser. No. 08/309,130 now U.S. Pat. No. 5,557,097, filed Sep. 20, 1994, entitled "Cytological System Autofocus Integrity Checking Apparatus," to Ortyn et al.; and issued U.S. patent application Ser. No. 08/308,140, filed Sep. 19, 1994, now U.S. Pat. No. 5,449,097 entitled "Automated Cytology System Position Integrity Checking Method and Apparatus" to Ortyn et al.

Figure 1B:
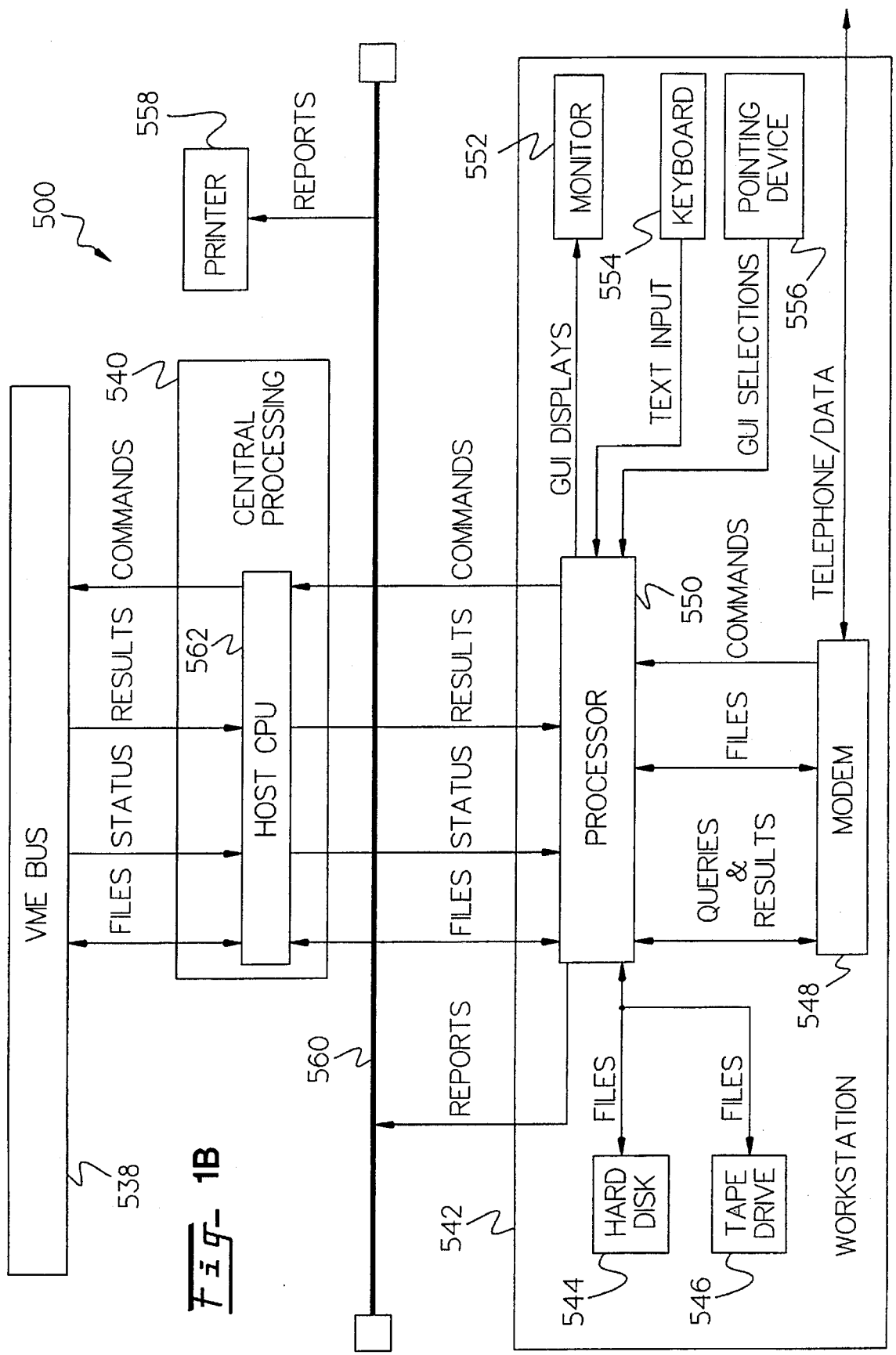
Figure 1C:
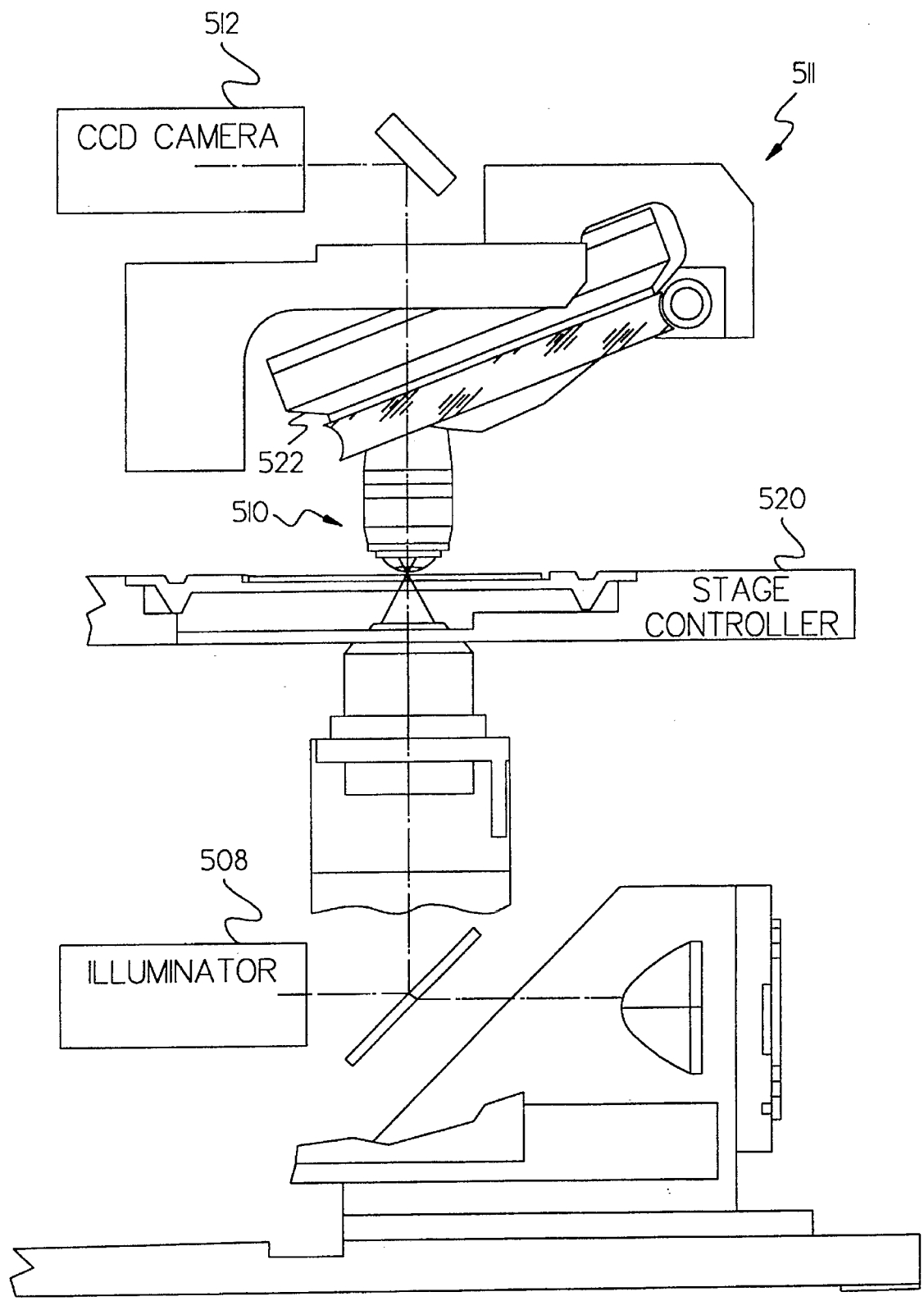

Now refer to FIGS. 1A, 1B and 1C which show a schematic diagram of one embodiment of the apparatus of the invention for integrating an automated biological screening system into a laboratory 500. The apparatus of the invention comprises an imaging system 502, a motion control system 504, an image processing system 536, a central processing system 540, and a workstation 542. The imaging system 502 is comprised of an illuminator 508, imaging optics 510, a CCD camera 512, an illumination sensor 514 and an image capture and focus system 516. The image capture and focus system 516 provides video timing data to the CCD cameras 512, the CCD cameras 512 provide images comprising scan lines to the image capture and focus system 516. An illumination sensor intensity is provided to the image capture and focus system 516 where an illumination sensor 514 receives the sample of the image from the optics 510. In some embodiments optics 510 may comprise color filters. In one embodiment of the invention, the optics may further comprise an automated microscope 511. The illuminator 508 provides illumination of a slide. The image capture and focus system 516 provides data to a VME bus 538. The VME bus distributes the data to an image processing system 536. The image processing system 536 is comprised of field-of-view processors 568. The images are sent along the image bus 564 from the image capture and focus system 516. A central processor 540 controls the operation of the invention through the VME bus 538. In one embodiment the central processor 562 comprises a MOTOROLA 68030 CPU. The motion controller 504 is comprised of a tray handler 518, a microscope stage controller 520, a microscope turret 522, and a calibration slide 524. The motor drivers 526 position the slide under the optics. A bar code reader 528 reads a barcode located on the slide 524. A touch sensor 530 determines whether a slide is under the microscope objectives, and a door interlock 532 prevents operation in case the doors are open. Motion controller 534 controls the motor drivers 526 in response to the central processor 540. An Ethernet communication system 560 communicates to a workstation 542 to provide control of the system. A hard disk 544 is controlled by workstation 550. In one embodiment, workstation 550 may comprise a workstation. A tape drive 546 is connected to the workstation 550 as well as a modem 548, a monitor 552, a keyboard 554, and a mouse pointing device 556. A printer 558 is connected to the ethernet 560.

During operation, the central computer 540, running a real time operating system, controls the microscope 511 and the processor to acquire and digitize images from the microscope 511. The flatness of the slide may be checked, for example, by contacting the four corners of the slide using a computer controlled touch sensor. The computer 540 also controls the microscope 511 stage to position the specimen under the microscope objective, and from one to fifteen field of view (FOV) processors 568 which receive images under control of the computer 540.

It is to be understood that the various processes described herein may be implemented in software suitable for running on a digital processor. The software may be embedded, for example, in the central processor 540.

In one mode of operation, a biological specimen such as a Pap smear is loaded to a slide processing system. The system processes a slide and generates an analysis score. In one preferred embodiment of the implementation, the analysis score is generated by the method disclosed in the pending U.S. patent application entitled "Method for Identifying Normal Biomedical Specimens" to Alan C. Nelson et al. referred to hereinabove. The analysis score is then thresholded. The slides having an analysis score less than a normal threshold are classified as normal slides which can be reported as normal without human intervention. The slides having an analysis score greater than or equal to the review threshold are the potentially abnormal slides. These slides require an independent microscopy review by a human. FIG. 2 shows a process flow diagram of the slide sorting data flow. A slide set is provided in step 300 and provided to a slide processing module 302. The slide processing module processes each slide and provides an analysis score in step 302. Decision logic is applied to the analysis score for each slide in step 304. The decision logic categorizes each slide as either clearly normal or requiring microscopy review. The decision logic is:

IF analysis score<normal threshold THEN normal ELSE microscopy review.

Figure 3:
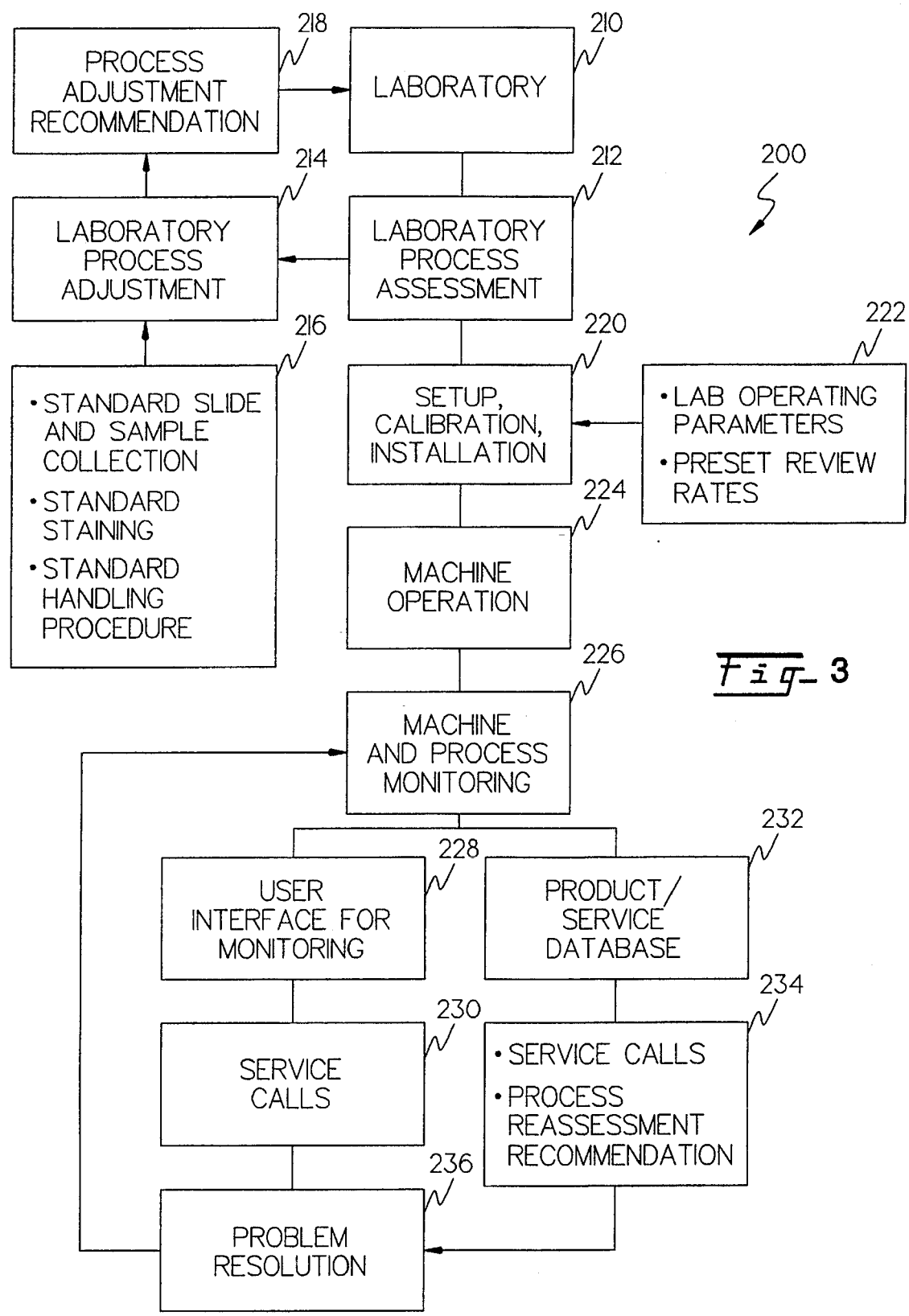
FIG. 3 shows a process flow diagram of the method for integrating an automated biological screening system of the invention.

Refer now to FIG. 3 which shows a process flow diagram of the method for integrating an automated biological screening system of the invention 200. The method makes a determination of a laboratory's cytological practices to improve effective operation of a selected automated biological screening system. The method of the invention begins with selection of a laboratory 210. The laboratory 210 selected could be, for example, a clinical laboratory, research laboratory, or a cytological laboratory for the screening of cervical Pap smears. A representative slide set is obtained from the selected laboratory. An example of a slide set is described below. The invention then performs a laboratory process assessment in step 212. The laboratory process assessment step 212 evaluates the suitability of a laboratory's slide population and cytology practices for effective processing by an automated biological screening system such the Autopap 300 or similar system. Depending on the result of the laboratory process assessment step 212, the method proceeds to the laboratory process adjustment step 214, or to setup, calibration, and installation of the preselected automated biological screening system in step 220.

The laboratory process adjustment step 214 receives standardized input from step 216, which in one preferred embodiment comprises standard slide and biological sample collection, standard staining and standard handling procedures. The laboratory process adjustment step 214 compares and assesses the data from the laboratory process assessment step 212 and makes a process adjustment recommendation in step 218. The process adjustment recommendations determined in step 218 may be incorporated in whole or in part by the selected laboratory 210. A sample slide set representative of the current laboratory technique is obtained from the preselected laboratory 210 and undergoes the laboratory process assessment step 212. Depending upon the data generated by the laboratory process assessment step 212, either the laboratory process adjustment step 214 is repeated, or the method proceeds to setup, calibration, and installation of the preselected automated biological screening system in step 220.

The setup, calibration and installation of the preselected automated biological screening system step 220 includes input of selected parameters in step 222, which in one preferred embodiment include lab operating parameters such as the review rate, as described in greater detail with reference to FIG. 5. The review rate is defined as the percent of slides requiring microscopy review. The preselected automated biological screening system may then be put into operation in step 224. Machine and process monitoring continues during operation of the automated system in step 226. In one preferred embodiment, the machine and process monitoring step 226 includes system integrity checks and machine and process monitoring checks. The method further provides for a user interface for monitoring in step 228. If the method determines a machine or process failure, then a service call can be triggered in step 230 depending on the severity of the machine failure, at other times a reboot of the machine is required. The re-calibrate or reboot of the machine can be automatic or requested by the user. The method also provides for monitoring of the automated system during operation while it processes data. The automated system processing data is continuously updated and is optionally stored in a product/service database at a central monitoring center in step 232. The automated system processing data transfers data through either a modem, tape or other transferrable media. Data indicating a machine or process failure triggers a response in step 234, which in one preferred embodiment comprises a service call or a process reassessment recommendation. A technician initiates problem resolution in step 236, if required, according to the result in steps 230 and 234. The process then returns to step 226 for continued machine and process monitoring.

The method for integrating an automated biological screening system of the invention comprises four major components. Table 1 provides a summary of these components and their functions.

TABLE 1

| | |
|---|---|
| Laboratory Process Assessment | Evaluates the compatibility of a laboratory's slide preparation and cytology practices with the application of an automated biological screening system. |
| Laboratory Process Adjustment | Improves the throughput and accuracy of the automated biological screening system's interpretation of the laboratory's slides. |
| System Setup, Calibration and Installation | Installs and qualifies the system, and adjusts the operational parameters of the automated biological screening system. |
| Machine and Process Monitoring | Continuously monitors the laboratory's processes and automated biological screening system to ensure integrity. |

Figure 4:
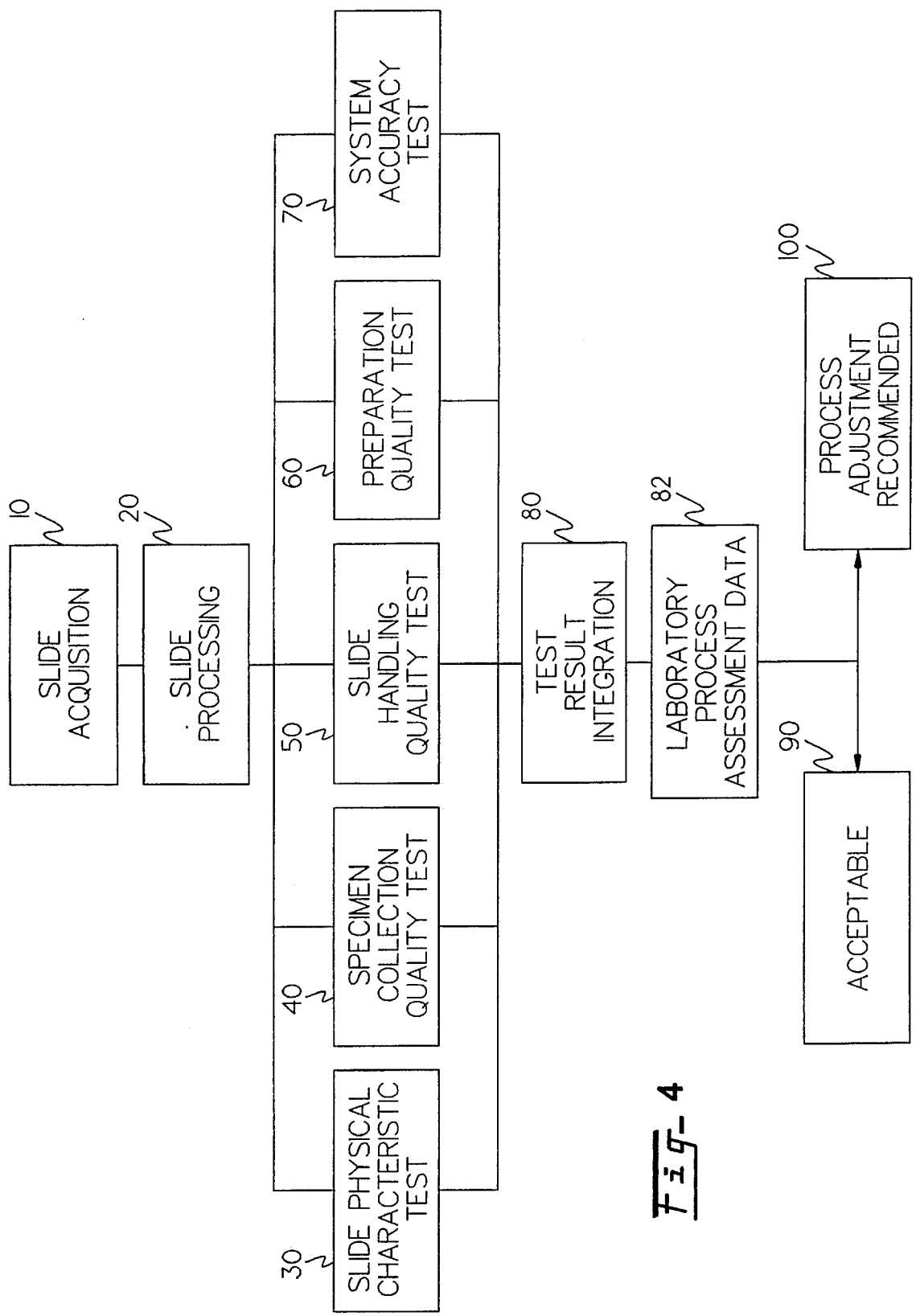
FIG. 4 shows a flow chart of the method for assessing laboratory processing quality of the invention.

Refer now to FIG. 4 which shows a process flow diagram of the laboratory process assessment step 212. A technician gathers a set of laboratory slides with representative normal and abnormal slides in step 10. Slides to be evaluated are from a selected laboratory. In the preferred embodiment, the assessor acquires 400 slides from the laboratory. The slide set comprises the following slides:

200 within normal limit slides, 150 low grade SIL slides, and 50 high grade SIL slides.

Low grade squamous intraepithelial lesions (SIL) and high grade squamous intraepithelial lesions are the extremes of a spectrum of lesions which may include noninvasive cervical epithelial abnormalities traditionally classified as flat condyloma, dysplasia/carcinoma in situ, and cervical intraepithelial neoplasia.

An automated system, such as, for example, is described in the referenced patents, processes the slide set to obtain data for assessing slide and specimen preparation quality in step 20. In one preferred embodiment, the automated system comprises the AutoPap® 300, available from NeoPath, Inc, located in Redmond, Wash. The automated system processes and obtains data from the acquired slides.

In steps 30–70, the automated system performs a series of tests on the data obtained in step 20. In step 30, the automated system performs a Slide Physical Characteristics Test to evaluate the physical characteristics of Pap Smear slides to determine if they can be successfully scanned by a predetermined automated biological specimen analyzer, such as the AutoPap® 300 System. The Slide Physical Characteristics Test evaluates the physical characteristics of the slides acquired from the laboratory. These physical characteristics include, for example, the characteristics shown in Table 2.

TABLE 2

Slide too thick
Unable to map coverslip surface
Coverslip edges not detected
Coverslip length not 40, 50, or 60 mm
Coverslip width not with limits
Coverslip corners not square
Coverslipped area too small
Coverslip skewed on slide
Unable to focus on specimen
Coverslip and specimen too thin
Coverslip and specimen too thick During evaluation, the automated system discontinues processing for slides that fall outside of an acceptable range for any of the preselected criteria. The automated system counts a proportion of slides failing processing. In one preferred embodiment, the slide set is considered to pass if the proportion of slides failing processing is less than 6%; otherwise the slide set fails.

In step 40, the automated system performs a specimen collection quality test to evaluate the quality and sufficiency of the specimen material sampled on the slide. Specimen collection quality is highly dependent upon a clinic's sampling tools and techniques for specimen collection. In the preferred embodiment, the Specimen Collection Quality Test comprises two tests. Tables 3 and 4 list qualities for which the slide set is tested. Slides failing these tests comprise the specimen collection quality failures. Table 3 tabulates slide set-up related failures. Table 4 tabulates failures related to process suitability failures. Process suitability failures include, for example, slides for which process results cannot be expected to be reliable, for example, when the process detects too few reference cells. The proportion of slides failing processing for these reasons is measured. In the preferred embodiment, if the proportion of slides that failed the first test is less than 7%, the slide set is considered to pass the first test; otherwise, the slide set fails.

In the preferred embodiment, the second specimen quality test measures and ranks the reference cell ratio for all normal slides. The reference cell ratio is the number of detected reference cells (that is, free-lying intermediate cells) on a slide divided by the number of all objects detected on the slide. In one preferred embodiment, if 85% of the normal slides have a reference cell ratio greater than 0.015, then the slide set is considered to pass the test; otherwise, the slide set fails.

The slide set is required to pass both specimen quality tests to pass the specimen collection quality test.

TABLE 3

Lack of material in center
Too few points for low-power focus map
Specimen distributed in small area
Unable to focus on specimen
Specimen tilt
Too few fields ranked in low-power scan
Too few points for high-power focus map
High-power focus surface too variable
Too few focused fields in high-power scan

TABLE 4

Insufficient reference cells
Image quality not within limits, percentage of fields focused on first try.
Image quality not within limits, percentage of fields never focused.

The automated system performs a Slide Handling Quality Test in step 50. The Slide Handling Quality Test determines if slide handling practices may need to be modified to facilitate effective processing on a selected automated system, such as the AutoPap® 300 System. The test evaluates the quality of slide barcoding, cleaning, and loading practices at a preselected clinical site. Tables 5 and 6 list tests for slide handling quality failures. Table 5 tabulates slide set-up related failures. Table 6 tabulates failures related to process suitability failures. The system measures the proportion of slides failing these tests. In the preferred embodiment, if the proportion of slides that failed is less than 5%, the slide set is considered to pass the slide handling quality test; otherwise, the slide set fails.

TABLE 5

Slide barcode not read
Slide tilted

TABLE 6

Image quality not within limits, excessive striping.
Image quality not within limits, high power magnification image saturation (small amounts)
Image quality not within limits, high power magnification image saturation (large amounts)
Image quality not within limits, low power magnification image saturation.

The automated system performs a Preparation Quality Test in step 60. The Preparation Quality Test evaluates the result of laboratory fixation, staining, and coverslipping processes to see if the presentation of cells is within an acceptable range. In the preferred embodiment, five tests comprise preparation quality test—to pass the full test, the slide set must pass all tests. Referring to Tables 7 and 8, slides which fail processing for the tabulated reasons comprise the preparation quality failures. The proportion of slides failing processing for these reasons is measured. Table 7 tabulates slide set-up related failures. Table 8 tabulates failures related to process suitability failures. In the preferred embodiment, if the proportion of slides that failed the first test is less than 5%, the slide set passes the first test; otherwise, the slide set fails.

TABLE 7

Too many bubbles
Too few fields ranked in low-power scan

TABLE 8

Stain average not within limits
Cytoplasm Staining not within limits
Staining detail not within limits
Nuclear/Cytoplasm contrast not within limits
Insufficient reference cells
Image quality not within limits, high power magnification image saturation (large amounts)
Image quality not within limits, low power magnification image saturation.

The second preparation quality test measures the nuclear stain density of the reference cells detected on the slide. Measurements are stored in a "mean stain" bin. The mean optical density for each detected intermediate cell nucleus is calculated. Data for all the detected intermediate cell nuclei on the slide is accumulated in a 10-bin histogram. The average staining score for the normal slides is calculated. In the preferred embodiment, if the average staining score is greater than 4.2 or less than 6.4, the slide set passes the test; otherwise, the slide set fails.

The third preparation quality test counts the number of potentially abnormal cell nuclei detected on a slide (stage 3 abnormals). The 80th percentile of the normal slides which contain endocervical component cells is calculated. In the preferred embodiment, if the 80th percentile is greater than 3, the slide set passes the test; otherwise, the slide set fails.

The fourth preparation quality test measures the 80th percentile of the QC score of the normal slides which contain endocervical component cells. In the preferred embodiment, if the 80th percentile is greater than 0.15 and less than 0.6, the slide set passes the test; otherwise, the slide set fails.

The fifth preparation quality test measures the median of reference cell nuclear texture (nuclear blur average) for the normal slides which contain endocervical component cells. In the preferred embodiment, if the median is greater than 5.65, the slide set passes the test; otherwise, the slide set fails.

In step 70, the automated system performs a Classification Test. The Classification Test evaluates whether the customer slide and cell presentation are within the training range of the AutoPap® 300 System to enable an effective interpretation by the system. The test evaluates the accuracy of slide classifications.

The system accuracy test evaluates sensitivity to abnormal specimen morphology. The 80th percentile of the QC score of the normal slides is calculated. In the preferred embodiment, if more than 70% of the low grade slides and 80% of the high grade slides have QC scores above the 80th percentile for normal slides, the slide set passes the test; otherwise, the slide set fails.

In step 80, the automated system then integrates the results from the tests in steps 30–70. The output from the test integration step 80 is the laboratory process assessment data step 82. In one embodiment the laboratory process assessment data step 82 indicates satisfactory laboratory processing in step 90 or may indicate at least one process failure. If the laboratory process assessment data indicates at least one process failure the laboratory process assessment data makes recommendations for adjustment of laboratory or clinic procedures in step 100.

Table 9 provides a summary of the five tests which, in one preferred embodiment, comprise the laboratory process assessment step 212.

TABLE 9

| Laboratory Process Assessment | |
|---|---|
| Test | Description |
| Slide Physical Characteristic Test | Evaluates the physical characteristics of Pap Smear slides to see if they can be successfully scanned by the AutoPap ® 300 System. |
| Specimen Collection Quality Test | Evaluates the quality and sufficiency of the cervical specimen material sampled. The success of the AutoPap ® 300 System processing is highly dependent upon the sampling tools and technique of the specimen collection. |
| Slide Handling Quality Test | Determines if a customer's slide handling practices can be modified to facilitate effective AutoPap ® 300 System processing. The test evaluates the quality of slide barcoding, cleaning, and loading practices in the customer sites. |
| Preparation Quality Test | Evaluates the result of laboratory fixation, staining, and coverslipping processes to see if the presentation of cells is within the acceptable range of the AutoPap ® 300 System. |
| Classification Test | Evaluates whether the customer slide and cell presentation are within the training range of the AutoPap ® 300 System to enable an effective interpretation by the system. The test evaluates the accuracy of slide classifications. |

Figure 5B:
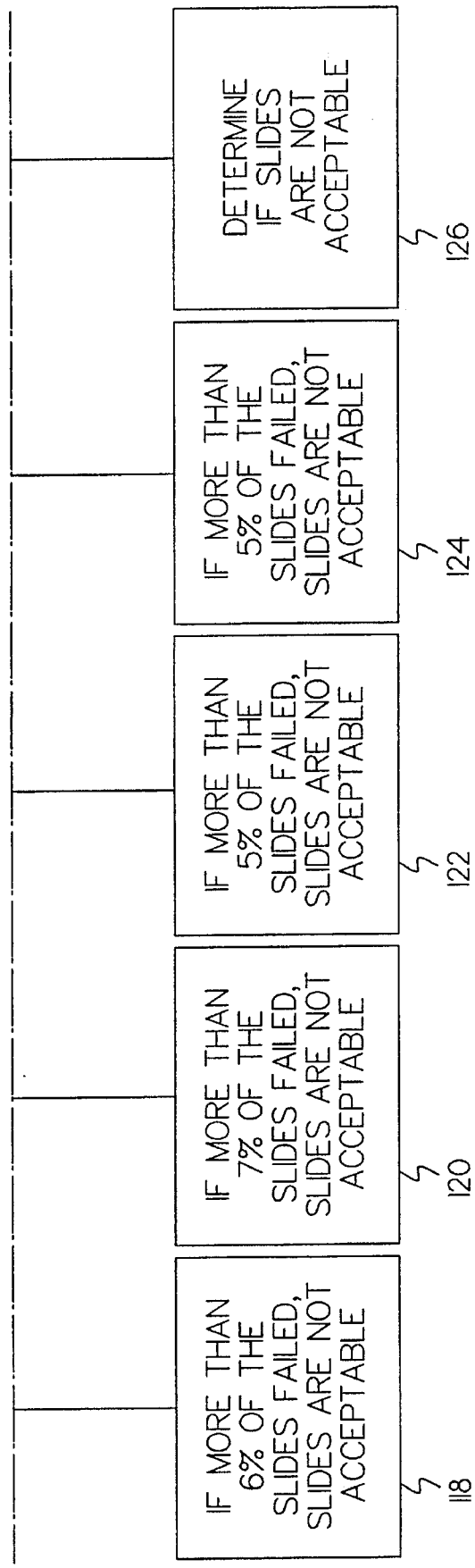
FIG. 5 shows a more detailed flow chart of the method for assessing slide and specimen preparation quality of the invention.

Now referring to FIG. 5, FIG. 5 shows a more detailed flow chart of the method for assessing slide and specimen preparation quality of the invention. In one embodiment of the invention slides are collected at step 102. At process step 104 the collected slides are cleaned and a barcode is affixed to the slides. At process step 106 the slides are processed in accordance with the various quality control methods described herein. Processing includes process steps through process step 126 as shown in FIG. 5 and as described with reference to the tables hereinbelow. At process step 108 a percentage of slides is determined as failing quality control processing for physical characteristics. At process step 118 slides are determined to be unacceptable as failing quality control processing for physical characteristics if more than 6% of the slides failed this test. At process step 110 a percentage of slides is determined as failing quality control processing for specimen collection characteristics. At process step 120 slides are determined to be unacceptable as failing quality control processing for specimen collection characteristics if more than 7% of the slides failed this test. At process step 112 a percentage of slides is determined as failing quality control processing for slide handling quality characteristics. At process step 122 slides are determined to be unacceptable as failing quality control processing for slide handling quality characteristics if more than 5% of the slides failed this test. At process step 114 a percentage of slides is determined as failing quality control processing for specimen preparation characteristics. At process step 124 slides are determined to be unacceptable as failing quality control processing for specimen quality characteristics if more than 5% of the slides failed this test. At process step 116 a percentage of abnormal slides is determined as scoring higher than the 80th percentile of normal specimens. At process step 126 slides are determined to be not acceptable if fewer than 70% of the low grade slides or fewer than 80% of the high grade slides have scores higher than the 80th percentile of normal specimens.

Figure 6:
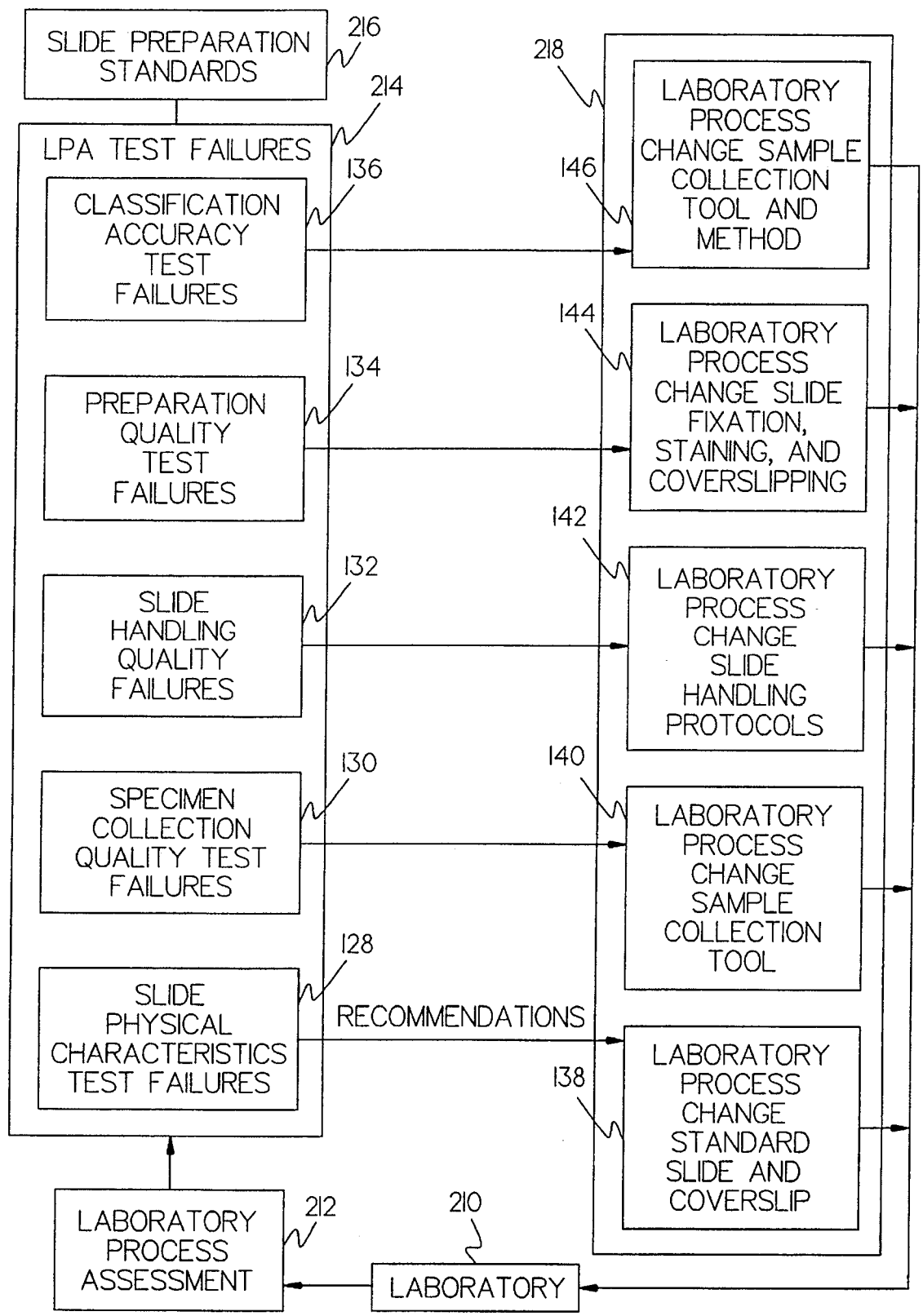
FIG. 6 shows a flow diagram of one embodiment of the laboratory process adjustment of the invention.

Now refer to FIG. 6 which shows a more detailed schematic diagram of one embodiment of the method of the invention to perform the laboratory process adjustment step 214 and the process adjustment recommendation step 218. The laboratory process adjustment step 214 improves the effectiveness of an automated biological screening system by applying a recommended set of slide preparation standards 216 to a laboratory's slide preparation process. The recommended standards 216 include but are not limited to slide and coverslip specifications, sample collection tools and techniques, staining and preparation processes, and slide handling procedures.

The laboratory process adjustment step 214 receives the data from the laboratory process assessment step 212. In one embodiment, the data from the laboratory process assessment comprise slide physical characteristics test failures 128, specimen collection quality test failures 130, slide handling quality failures 132, preparation quality test failures 134 and classification accuracy test failures 136. In one embodiment the laboratory process adjustment step 214 makes process adjustment recommendations in step 218 based on the data from the laboratory process assessment. The method of the invention provides recommendations to address specific failures. In one embodiment, the laboratory process adjustment step 214 makes a standard slide or coverslip recommendation 138 in response to a slide physical characteristics test failure 128, a sample collection tool recommendation 140 in response to a specimen collection quality test failure 130, a slide handling protocols recommendation 142 in response to a slide handling quality failure 132, a slide fixation, staining or coverslip affixing recommendation 144 in response to a preparation quality test failure 134 and a sample collection tool or method recommendation 146 in response to a classification accuracy test failure 136.

In one embodiment of the invention, laboratory process assessment test failures are confirmed by additional processing and characterizations; confirmation may further require evaluation of the selected laboratory's staining protocol and additional, specific types of slides.

Figure 7:
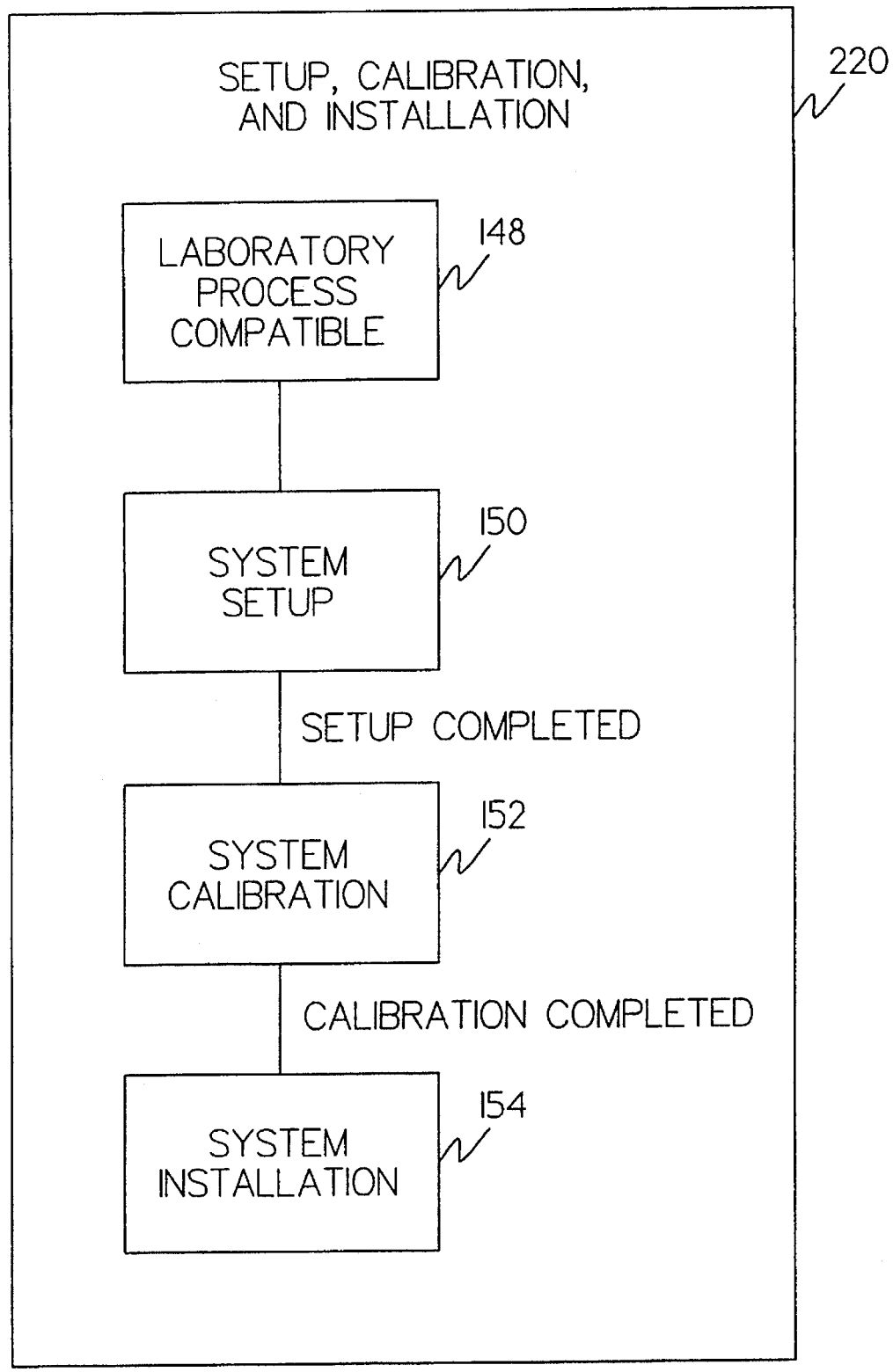
FIG. 7 shows a flow diagram of one embodiment of the setup, calibration and installation method of the invention.

Now refer to FIG. 7 which shows a flow diagram of one embodiment of the setup, calibration and installation process 220 of the invention. The laboratory process may be determined to be satisfactory in step 148 after completion of laboratory process assessment step 212 and laboratory process adjustment step 214. A technician may set up the automated biological screening system in the selected laboratory in step 150. The method optimizes throughput of the automated biological screening system by configuring the automated system as part of an overall laboratory cytology workflow process. The method further provides for optimization of system accuracy through calibration of machine parameters to match the laboratory operation parameters in step 152. In one embodiment, parameter calibration determines the most appropriate machine score threshold to obtain a desired slide review rate. During installation in step 154, the automated biological screening system is integrated with the laboratory workflow and qualified for routine operation.

Now refer to FIG. 8 which shows a flow diagram of machine and process monitoring 226 of the invention. After completion of setup, calibration and installation in step 156 and upon operation of the machine, the method provides for continuous and dynamic machine and laboratory process monitoring. The machine and process monitoring ensures that automated biological screening systems at laboratory sites continue to operate properly.

In one preferred embodiment of the invention, the process begins at step 158, where a batch of slides is run to determine machine operating and process parameters. The batch of slides is continually updated over time to provide a current assessment of automated system function and laboratory procedure. The slide processing 158 provides machine data for machine monitoring 160 and slide data for process monitoring 164. Machine monitoring 160 determines whether operating parameters from the machine data are within predetermined limits. Process monitoring 164 determines whether process parameters from the slide data are within predetermined limits. Machine operating parameters and laboratory process parameters are checked against their expected values, which are established during system setup, calibration and installation. For example, these parameners may include the following:

System integrity parameters;

Slide physical characteristics parameters;

Sample collection monitoring parameters;

Slide handling monitoring parameters; and

Preparation monitoring parameters.

In one preferred embodiment, machine monitoring 160 may include system integrity tests and machine monitoring software. The system integrity tests and machine monitoring software may perform continuous checks on the status of the automated system. If operating parameters are within predetermined limits, the method returns to slide processing 158. Otherwise, if operating parameter are determined to fall outside of the predetermined limits, the method flows to step 162 to perform operating parameter adjustment or field service as necessary. The automated biological screening system may include a calibration slide with a series of self tests and automatic calibration procedures that monitor and calibrate many crucial aspects of system performance in an on-going basis. The automated system may perform these tests and calibrations as often as every eight slides. The important operating parameters monitored as part of system integrity and calibrated include imaging resolution, focus, mechanical repeatability, image processing and illumination stability. The system integrity self checks and system calibrations assure that dirt, malfunction or drift have not affected the processing results of the automated biological screening system. In step 162, the automated biological screening system may be recalibrated to allow conditions that fall outside the acceptable range of the system as necessary. In one preferred embodiment, the automated system may allow the laboratory to access plots of certain parameters using the display window or the printer. The automated system may provide instruction for recovering from an out-of-range conditions or may trigger a call for field service.

Machine monitoring 160 and process monitoring 164 may further comprise transmitting the machine data and the slide data to a product/service center. Data may be transmitted through a modem connection or by shipping media. The data is processed and stored in a product/service database at the product/service center. If machine data and slide data are within predetermined bounds, the method returns to slide processing 158 for continued monitoring.

If machine monitoring 160 determines operating parameters to be outside predetermined bounds, the method may provide a parameter adjustment or, depending on severity, trigger a field service call. When operating parameters return to the predetermined limits, the method returns to slide processing 158 for continued monitoring.

If process monitoring 164 determines process parameters to be within predetermined bounds, the method returns to slide processing 158 for continued monitoring. If process monitoring 164 determines process parameters to be outside predetermined bounds, the method may determine a process parameter adjustment or, depending on severity of the condition, trigger a recommendation for an iteration of the laboratory process adjustment in step 166. When process parameters return to the predetermined limits, the method returns to slide processing 158 for continued monitoring.

Those skilled in the art will recognize that other types of automated biological inspection and screening systems are within the scope of the invention and that the invention is not limited to the automated system described herein.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method of integrating an automated biological screening system to a laboratory comprising the steps of:
   (a) obtaining a slide set from the laboratory;
   (b) gathering parameter data from the slide set wherein the parameter data is representative of the slide set;
   (c) measuring characteristics of the parameter data to provide a plurality of processing quality data outputs; and
   (d) integrating the plurality of processing quality data outputs with each other to provide a suitability assessment of the slide set, the suitability assessment indicating suitability for processing by the automated biological screening system.

2. The method of claim 1 wherein the step of integrating the plurality of processing quality data outputs further comprises the steps of:
   (i) measuring a laboratory process parameter derived from the parameter data from the slide set to provide laboratory process assessment data;
   (ii) providing a suitability assessment of laboratory processes based on the laboratory process assessment data; and
   (iii) independently adjusting the laboratory processes based upon the laboratory process assessment data.

3. The method of claim 2 wherein the step of independently adjusting the laboratory processes further comprises the step of providing at least one lab process parameter adjustment recommendation.

4. The method of claim 2 wherein the step of providing a suitability assessment of laboratory processes based upon the laboratory process assessment data further comprises the steps of:
   (a) evaluating preselected characteristics of the slide set; and
   (b) determining laboratory process quality by checking whether the preselected characteristics are within predetermined limits.

5. The method of claim 4 wherein the step of evaluating preselected characteristics of the slide set further comprises the step of evaluating physical characteristics of a slide from the slide set.

6. The method of claim 4 wherein the step of evaluating preselected characteristics of the slide set further comprises the step of evaluating system accuracy.

7. The method of claim 4 wherein the step of evaluating preselected characteristics of the slide set further comprises the step of evaluating specimen material of a slide from the slide set.

8. The method of claim 4 wherein the step of evaluating preselected characteristics of the slide set further comprises the step of evaluating handling quality of a slide from the slide set.

9. The method of claim 4 wherein the step of evaluating preselected characteristics of the slide set further comprises the step of evaluating preparation quality of a slide from the slide set.

10. The method of claim 2 wherein the step of independently adjusting the laboratory processes further comprises the steps of:
    a) comparing the laboratory process assessment data to a set of predetermined standards to provide a discrepancy output; and
    b) determining at least one process adjustment recommendation based on the discrepancy output.

11. The method of claim 2 further including the step of adjusting the laboratory processes until the laboratory process assessment data are within a predetermined range.

12. The method of claim 2 wherein the step of independently adjusting the laboratory processes further comprises the step of making a standard slide and coverslip recommendation when the laboratory process assessment data indicate a slide physical characteristics test failure.

13. The method of claim 2 wherein the step of independently adjusting the laboratory processes further comprises the step of making a sample collection tool recommendation when the laboratory process assessment data indicate a specimen collection quality test failure.

14. The method of claim 2 wherein the step of independently adjusting the laboratory processes further comprises the step of making a method recommendation when the laboratory process assessment data indicate a specimen collection quality test failure.

15. The method of claim 2 wherein the step of independently adjusting the laboratory processes further comprises the step of making a slide handling protocols recommendation when the laboratory process assessment data indicate a slide handling quality failure.

16. The method of claim 2 wherein the step of independently adjusting the laboratory processes based upon the laboratory process assessment data further comprises the step of making a slide fixation recommendation when the laboratory process assessment data indicate a preparation quality test failure.

17. The method of claim 2 wherein the step of independently adjusting the laboratory processes based upon the laboratory process assessment data further comprises the step of making a specimen staining recommendation when the laboratory process assessment data indicate a preparation quality test failure.

18. The method of claim 2 wherein the step of independently adjusting the laboratory processes based upon the laboratory process assessment data further comprises the step of making a coverslip affixing recommendation when the laboratory process assessment data indicate a preparation quality test failure.

19. The method of claim 2 wherein the step of independently adjusting the laboratory processes based upon the laboratory process assessment data further comprises the step of making a sample collection tool recommendation when the laboratory process assessment data indicate a classification accuracy test failure.

20. The method of claim 2 wherein the step of independently adjusting the laboratory processes based upon the laboratory process assessment data further comprises the step of making a sample collection method recommendation when the laboratory process assessment data indicate a classification accuracy test failure.

21. The method of claim 1 further comprising the step of calibrating the automated biological screening system in response to the plurality of processing quality data outputs.

22. The method of claim 21 wherein the step of calibrating the automated biological screening system further comprises the step of providing an interface for adjusting system parameters.

23. The method of claim 21 wherein the automated biological screening system includes an imaging system, an image processing system, and a central processing system that are characterized by machine operating parameters, and wherein the method further comprises the step of adjusting the machine operating parameters according to the laboratory process assessment data.

24. The method of claim 23 wherein the step of calibrating the automated biological screening system further comprises the step of calibrating machine operating parameters to obtain a desired slide microscopy review rate.

25. The method of claim 1 wherein the automated biological screening system includes an imaging system, an image processing system, and a central processing system that are characterized by machine operating parameters, further comprising the step of measuring at least one machine operating parameter using the image data from the slide set, at intervals, to provide at least one operating parameter of the automated biological screening system.

26. The method of claim 25 further comprising the step of displaying the at least one operating parameter.

27. The method of claim 25 wherein the intervals comprise periodic time intervals.

28. The method of claim 25 wherein the intervals comprise random time periods.

29. The method of claim 25 wherein the intervals are based on the number of slides examined.

30. The method of claim 25 further comprising the step of storing the at least one operating parameter in a database.

31. The method of claim 1 further comprising the steps of measuring at least one laboratory process parameter, at intervals, based on at least one recent slide set processed by the automatic biological screening system to provide at least one laboratory process monitoring parameter.

32. The method of claim 31 further comprising the step of displaying the at least one laboratory process monitoring parameter.

33. The method of claim 31 further comprising the step of providing at least one parameter adjustment recommendation.

34. The method of claim 31 wherein the intervals are time periods that are periodic.

35. The method of claim 31 wherein the intervals are time periods that are random.

36. The method of claim 31 wherein the intervals are based on the number of slides examined.

37. The method of claim 31 further comprising the step of adjusting laboratory processes based upon the at least one laboratory process monitoring parameter.

38. The method of claim 31 further comprising the step of calibrating the automated biological screening system.

39. The method of claim 31 further comprising the step of storing the at least one laboratory process monitoring parameter in a database.

40. The method of claim 31 wherein the automated biological screening system includes an imaging system, an image processing system, and a central processing system that are characterized by machine operating parameters, further comprising the step of measuring at least one machine operating parameter, at intervals, based on the at least one recent slide set to provide at least one operating parameter of the automated biological screening system.

41. The method of claim 1 wherein the step of obtaining a slide set from the laboratory further comprises the steps of obtaining slides representative of a predetermined laboratory slide population.

42. An apparatus for integrating an automated biological screening system to a laboratory comprising:
(a) a means for automated biological screening providing a biological data output;
(b) a means for assessing laboratory processes connected to receive the biological data output and providing a laboratory process assessment output wherein the means for assessing laboratory process further comprises;
  (i) a means for gathering image data representative of a population of slides from the laboratory and providing an image data output;
  (ii) a means for determining processing quality data connected to receive the image data output and providing a plurality of processing quality data outputs; and
  (iii) a data processing system connected to receive and integrate the plurality of processing quality data outputs with each other, wherein the data processing system provides a population suitability data output based on the plurality of processing quality data outputs, where the population suitability data output provides an indication of the suitability of the laboratory's slide population for processing by an automated biological screening system;
(c) a means for adjusting laboratory processes connected to receive the laboratory process assessment output wherein the means for adjusting laboratory process further includes means for providing a process adjustment recommendation;
(d) a means for setup, calibration and installation of the automated biological screening system connected to receive the laboratory process assessment output and providing a calibration parameter output; and
(e) a means for monitoring operation of the automated biological screening system connected to receive the biological data output and the calibration parameter output and providing a laboratory process monitoring output.

43. The apparatus of claim 42 wherein the means for determining processing quality data further comprises a means for testing slide physical characteristics connected to receive the image data output and providing slide physical characteristics data output.

44. The apparatus of claim 42 wherein the means for determining processing quality data further comprises a means for testing specimen material quality connected to receive the image data output and providing specimen material quality data output.

45. The apparatus of claim 42 wherein the means for determining processing quality data further comprises a means for testing slide handling quality connected to receive the image data output and providing slide handling quality data output.

46. The apparatus of claim 42 wherein the means for determining processing quality data further comprises a means for testing slide preparation quality connected to receive the image data output and providing slide preparation quality data output.

47. The apparatus of claim 42 wherein the means for determining processing quality data further comprises a means for testing system accuracy connected to receive the image data output and providing system accuracy data output.

48. The apparatus of claim 42 wherein the means for gathering image data further comprises an automated microscope.

49. The apparatus of claim 42 wherein the means for assessing laboratory processes and the means for adjusting laboratory processes further comprise a central processor.

50. The apparatus of claim 42 wherein the means for monitoring operation of the automated biological screening system further comprises resident machine monitoring software and system integrity checks.

51. An apparatus for integrating an automated biological screening system to a laboratory comprising:

(a) a means for automated biological screening providing a biological data output;

(b) a means for assessing laboratory processes connected to receive the biological data output and providing a laboratory process assessment output;

(c) a means for adjusting laboratory procedures connected to receive the laboratory process assessment output and providing a process adjustment recommendation, wherein the means for adjusting laboratory procedures further comprises a databank of standard laboratory procedures and the process adjustment recommendation is selected from the databank of standard laboratory procedures;

(d) a means for setup, calibration and installation of the automated biological screening system connected to receive the laboratory process assessment output and providing a calibration parameter output; and (e) a means for monitoring operation of the automated biological screening system connected to receive the biological data output and the calibration parameter output and providing a system status output.

52. The apparatus of claim 51 wherein the means for monitoring further comprises a product/service database for storing a plurality of system status outputs from the monitoring means.

* * * * *

UNITED STATES PATENT AND TRADEMARK OFFICE
CERTIFICATE OF CORRECTION

PATENT NO.   :   5,619,428
DATED        :   April 8, 1997
INVENTOR(S)  :   Lee et al.

It is certified that error appears in the above-identified patent and that said Letters Patent is hereby corrected as shown below:

Column 10, line 47, after the word "steps" insert -- 108 --.

Signed and Sealed this

Eighteenth Day of August, 1998

Attest:

BRUCE LEHMAN

*Attesting Officer*        *Commissioner of Patents and Trademarks*